(12) United States Patent
Cheng et al.

(10) Patent No.: US 9,392,938 B2
(45) Date of Patent: Jul. 19, 2016

(54) OPHTHALMOSCOPE

(71) Applicant: Medimaging Integrated Solution, Inc., Hsinchu (TW)

(72) Inventors: Chu-Ming Cheng, Hsinchu (TW); Long-Sheng Liao, Hsinchu (TW); Yi-Wen Chen, Hsinchu (TW); Pin-Tseng Liu, Hsinchu (TW)

(73) Assignee: MEDIMAGING INTEGRATED SOLUTION, INC., Hsinchu (TW)

( * ) Notice: Subject to any disclaimer, the term of this patent is extended or adjusted under 35 U.S.C. 154(b) by 0 days.

(21) Appl. No.: 14/661,416

(22) Filed: Mar. 18, 2015

(65) Prior Publication Data

US 2016/0128569 A1    May 12, 2016

(30) Foreign Application Priority Data

Nov. 6, 2014    (TW) .............................. 103138490 A

(51) Int. Cl.
*A61B 3/14*    (2006.01)
*A61B 3/12*    (2006.01)
*A61B 3/00*    (2006.01)

(52) U.S. Cl.
CPC ................. *A61B 3/12* (2013.01); *A61B 3/0008* (2013.01); *A61B 3/14* (2013.01)

(58) Field of Classification Search
USPC ........................................................ 351/206
See application file for complete search history.

*Primary Examiner* — Jack Dinh
(74) *Attorney, Agent, or Firm* — Muncy, Geissler, Olds & Lowe, P.C.

(57) ABSTRACT

An ophthalmoscope comprises an illumination element providing an illumination light beam to illuminate the fundus of an eyeball; an imaging lens group converging the reflected light beam from the fundus; and an image capture module. The image capture module includes an image sensing element, a fixation light element and an optical element. The image sensing element captures the reflected light beam converged by the imaging lens group to form an image. The fixation light element provides a fixation light beam passing through the imaging lens group and reaching the fundus. The optical element is arranged among the imaging lens group, image sensing element and fixation light element to make the image sensing element and the fixation light element on different equivalent focal planes of the imaging lens group. According to the above-mentioned structure, a relay lens and a focusing module used by the conventional fixation light element is omitted.

16 Claims, 3 Drawing Sheets

US 9,392,938 B2

OPHTHALMOSCOPE

BACKGROUND OF THE INVENTION

1. Field of the Invention

The present invention relates to an ophthalmoscope, particularly to an ophthalmoscope having a fixation light source.

2. Description of the Prior Art

The ophthalmoscope is an instrument for inspecting the fundus of an eyeball, including the retina, the optic disc, and the vasculature. The fixation light source guides the eyeball to rotate to a special direction, enabling the inspector to observe the desired area. In the conventional ophthalmoscope, the fixation light is directed to the imaging system by an independent relay lens and then projected onto the fundus of the eyeball. Besides, the fixation light is projected to different focuses for different subjects by a focusing module. Consequently, more lenses and components are used by the conventional ophthalmoscope, hindering compactness and increasing the assembly cost.

Therefore, the manufacturers are eager to decrease the lenses and components of an ophthalmoscope so as to compact the structure of the ophthalmoscope.

SUMMARY OF THE INVENTION

The present invention provides an ophthalmoscope, which uses appropriate optical elements to make the image sensing element and the fixation light element situated on equivalent focal planes of the imaging lens group, whereby the fixation light element projects the fixation light beam onto the fundus of the eyeball via sharing the lens group and focusing mechanism of the imaging system.

In one embodiment, the ophthalmoscope of the present invention comprises an illumination element, an imaging lens group and an image capture module. The illumination element provides an illumination light beam passing through the pupil of an eyeball and reaching the fundus of the eyeball. The imaging lens group converges the reflected light beam from the fundus of the eyeball. The image capture module includes an imaging sensing element, a fixation light element and an optical element. The image sensing element captures the reflected light beam converged by the imaging lens group to form an image. The fixation light element and the image sensing element are arranged at an identical side of the imaging lens group. The fixation light element provides a fixation light beam passing through the imaging lens group and reaching the fundus of the eyeball. The optical element is arranged between the imaging lens group and the fixation light element and makes the image sensing element and the fixation light element situated on equivalent focal planes of the imaging lens group.

Below, the embodiments are described in detail in cooperation with the attached drawings to make easily understood the objectives, technical contents, characteristics and accomplishments of the present invention.

DESCRIPTION OF THE PREFERRED EMBODIMENT

Figure 1:
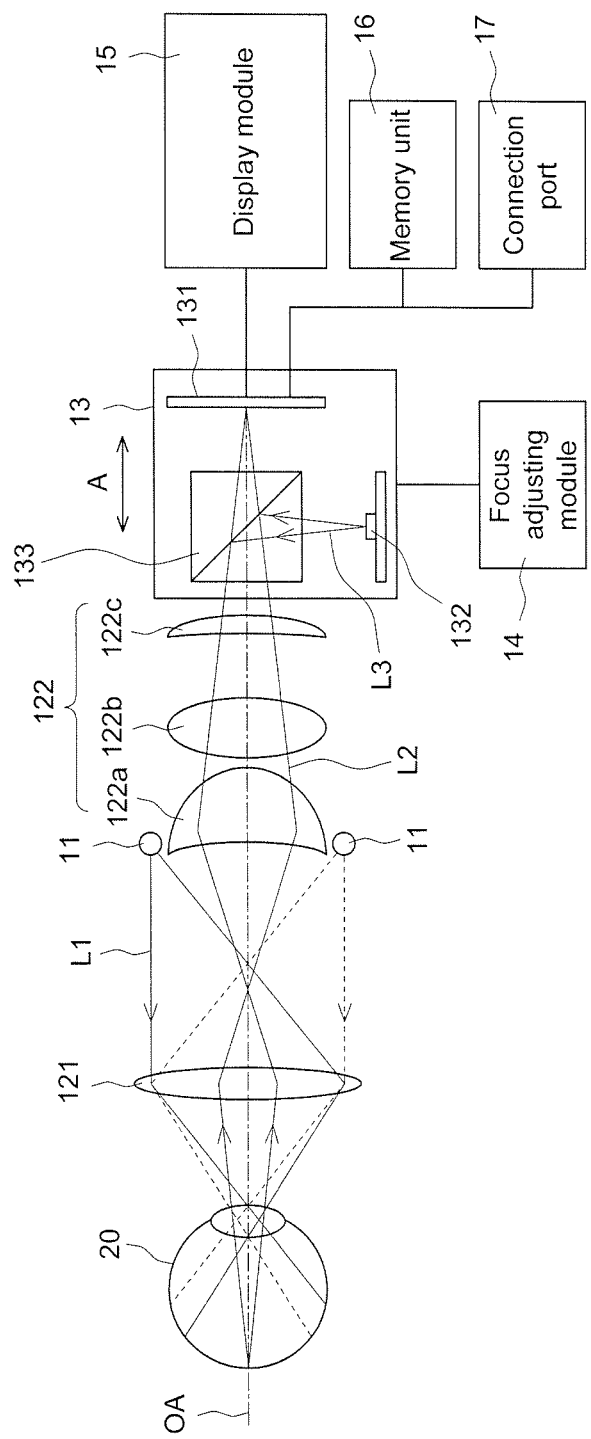
FIG. 1 schematically shows an ophthalmoscope according to one embodiment of the present invention.
Figure 5:
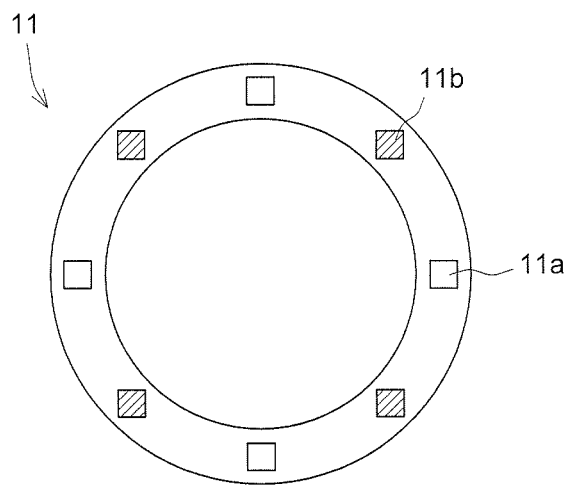
FIG. 5 schematically shows an illumination element according to one embodiment of the present invention.

Referring to FIG. 1, in one embodiment of the present invention, the ophthalmoscope comprises an illumination element 11, an imaging lens group and an image capture module 13. The illumination element 11 provides an illumination light beam L1 passing through the pupil of an eyeball 20 and reaching the fundus of the eyeball 20. In one embodiment, the light path of the illumination element 11 is deviated from the optical axis OA of the imaging lens group. In one embodiment, the illumination element 11 is an annular light emitting element (such as an organic light emitting diode (OLED)) or includes a plurality of light emitting elements (such as light emitting diodes (LED)) arranged annularly and symmetrically; the optical axis OA of the imaging lens group passes through the center of the annular shape. In one preferred embodiment, the illumination light beam L1 of the illumination element 11 provides direct illumination. The term "direct illumination" used herein means that all or most of the light generated by the light source is directly incident onto the fundus of the eyeball 20 without reflection by any artificial manipulation surface. Referring to FIG. 5, in one embodiment, the illumination element 11 has a plurality of first LEDs 11a and a plurality of second LEDs 11b; the first LEDs 11a are symmetrically and annularly arranged, and the second LEDs 11b are also symmetrically and annularly arranged; the central wavelength of the light emitted by the first LEDs 11a is different from the central wavelength of the light emitted by of the second LEDs 11b. For example, the first LEDs 11a emit visible light, such as white light, and the second LEDs 11b emit infrared light, respectively for different types of observations.

The imaging lens group has a first lens group 121 and a second lens group 122. The illumination light beam L1 passes through the first lens group 121 and reaches the fundus of the eyeball 20. In one embodiment, the position of the illumination element 11 and the position of the pupil meet an image-object relationship with respect to the first lens group 121. In other words, the height of the image can be adjusted to be smaller than the radius of the pupil to greatly increase the illumination efficiency via modifying the distance from the illumination element 11 to the optical axis OA and the distance from the illumination element 11 to the first lens group 121. According to the above-mentioned scheme, no relay lens between the illumination element 11 and the first lens group 121 is needed. In other words, the illumination light beam L1 of the illumination element 11 can be effectively utilized without any intermediate image.

The imaging lens group converges the reflected light beam L2 from the fundus of the eyeball 20 and form an image on the image capture module 13. The image capture module 13 includes an image sensing element 131, a fixation light element 132 and an optical element 133. The image sensing element 131 captures the reflected light beam L2 converged by the imaging lens group to form an image. In some embodiments, the image sensing element 131 is realized by CCD (Charge Coupled Device), a CMOS (Complementary Metal Oxide Semiconductor) sensor, or a photographic film. The fixation light element 132 and the image sensing element 131 are arranged at an identical side of the imaging lens group. The fixation light element 132 provides a fixation light beam L3 passing through the imaging lens group and reaching the fundus of the eyeball 20. The optical element 133 is arranged among the imaging lens group, the image sensing element 131 and the fixation light element 132 and makes the image sensing element 131 and the fixation light element 132 on equivalent focal planes of the imaging lens group. In some embodiments, the optical element 133 is a prism group (as shown in FIG. 1) or an optical splitter. However, an optical splitter may generate double images because of secondary reflection. Therefore, a prism group can achieve better image quality.

Figure 2:
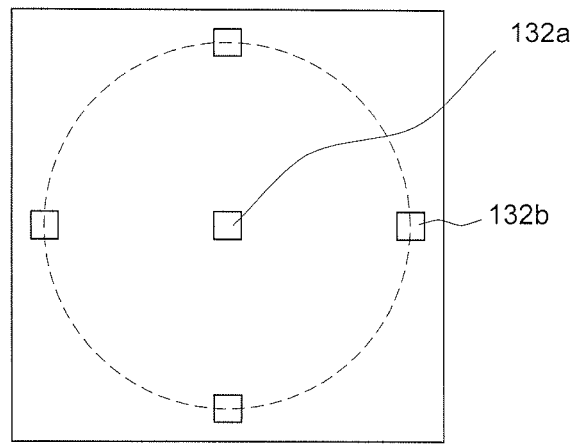
FIG. 2 schematically shows a fixation light element of an ophthalmoscope according to one embodiment of the present invention.
Figure 3:
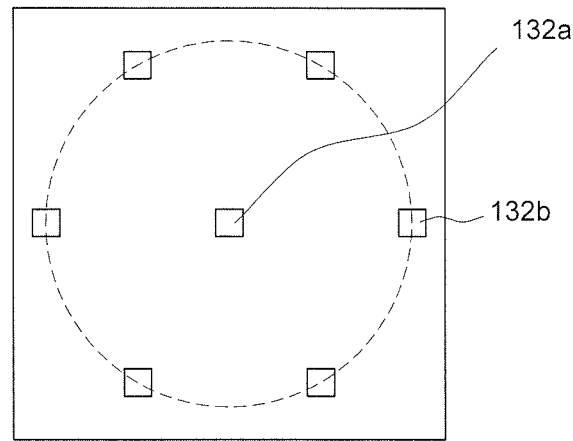
FIG. 3 schematically shows a fixation light element of an ophthalmoscope according to another embodiment of the present invention.
Figure 4:
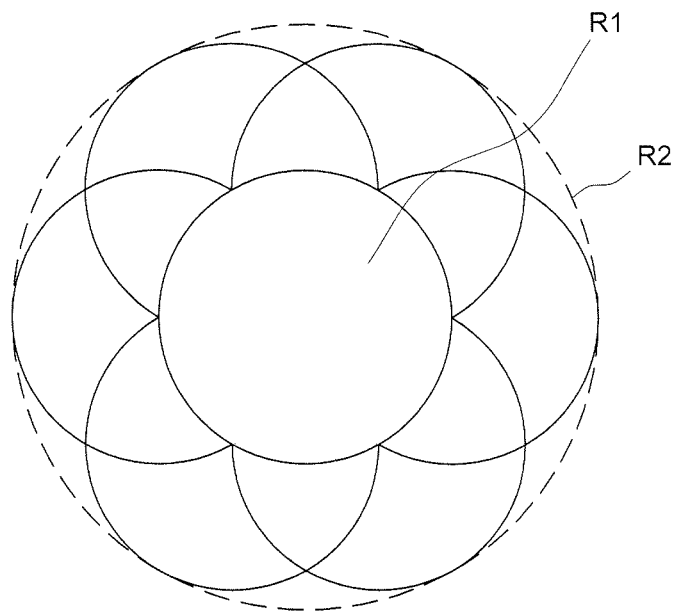
FIG. 4 schematically shows areas observable by the inspector using the fixation light element shown in FIG. 3.

Referring to FIG. 2, in one embodiment, the fixation light element 132 includes a first LED 132a and at least four second LEDs 132b. The second LEDs 132b are arranged annularly and symmetrically about the first LED 132a. In one preferred embodiment, the fixation light element 132 includes a first LED 132a and six second LEDs 132b; the six second LEDs 132b are arranged annularly and symmetrically about the first LED 132a, as shown in FIG. 3. FIG. 4 shows the areas observable by the inspector while the subject is guided by the fixation light element shown in FIG. 3. If the subject gazes at the center, the area observable by the inspector is merely the region designated by R1. If the subject is guided by the fixation light beam L3 to rotate his eyeball 20 to specific directions, the area observable by the inspector is the region designated by R2. It should be easily appreciated that the images obtained by rotating the eyeball to different directions can be integrated into a larger image.

According to the above-mentioned scheme, the fixation light beam L3 of the fixation light element 132 can pass through the imaging lens group and reach the fundus of the eyeball 20 without any extra relay lens. Besides, the fixation light element 132 and the image sensing element 131 are on equivalent focal planes of the imaging lens group. In other words, while the image sensing element 131 is on a focal plane of the imaging lens group, the fixation light element 132 must be on an equivalent focal plane of the imaging lens group. It should be easily appreciated that the optical effect is unchanged while the positions of the image sensing element 131 and the fixation light element 132 are exchanged.

In one embodiment, the ophthalmoscope of the present invention further comprises a focus adjusting module 14, which mechanically or electronically drives the image capture module 13 to move linearly along the optical axis OA of the imaging lens group 13 to attain an appropriate focal length, as indicated by the arrow A in FIG. 1. As the focus adjusting module 14 moves the image capture module 13 linearly, the user can arbitrarily vary the back focus of the imaging lens group without using other focus adjusting mechanisms, especially the nonlinear-compensation cam ring. Therefore, the imaging lens group is simplified and allowed to have a greater tolerance. Thus is reduced the difficulty and cost of fabricating the imaging lens group. In one embodiment, the focus adjusting module 14 also drives at least one of the lenses 122a, 122b and 122c of the image lens group to move linearly along the optical axis OA of the imaging lens group to adjust the focal length. It may be appreciated that while the fundus is imaged on the image sensing element 131, the fixation light element 132 is also imaged on the fundus owing to the fact that the fixation light element 132 and the image sensing element 133 have identical relative positions with respect to the optical element 133 or are on equivalent focal planes. Therefore, the action of adjusting the focal length of the image sensing element 131 according to the vision of the subject is equal to the action of adjusting the focal length of the fixation light element 132. Thus, it is unnecessary to additionally design a focus adjusting mechanism for the fixation light element 132. In one embodiment, the focus adjusting module 14 has an automatic focusing mechanism, wherein the fixation light beam L3 of the fixation light element 132 functions as the light source for automatic focusing, and the image sensing element 131 functions as a sensor for automatic focusing so as to provide feedback signals for the focus adjusting module 14 to undertake automatic focusing. In one alternative embodiment, the first LED 132a shown in FIG. 2 or FIG. 3 is replaced with a light sensing element to provide the feedback signals required by the focus adjusting module 14 in automatic focusing.

In one embodiment, the ophthalmoscope of the present invention further comprises a display module 15, which displays the image captured by the image capture module 13. It should be easily appreciated by the persons skilled in the art that the ophthalmoscope of the present invention may be applied for a processing unit for computation, which is integrated with or separated from the image capture module 13. The processing unit processes the image captured by the image capture module 13, including filtering noise, modifying contrast, and adjusting brightness. Then, the processing unit presents the image on the display module 15. Since the technology of the processing unit has been well known by the persons skilled in the art, it will not be described in detail herein.

In one embodiment, the ophthalmoscope of the present invention further comprises a memory unit 16 connected with the image capture module 13 and configured for recording the images captured by the image capture module 13, whereby to exempt the inspector (such as a physician) from drawing the inspection result of an subject (such as a patient) in hand and avoid the human error thereof. In one embodiment, the memory unit 16 is a flash memory, a hard disc drive or a combination thereof. For example, the memory unit 16 is a memory card.

In one embodiment, the ophthalmoscope of the present invention further comprises a connection port 17, whereby the ophthalmoscope may be physically connected with an external electronic device (not shown in the drawings) to transmit the images captured by the image capture module 13 to the external electronic device. In one embodiment, the connection port 17 is a Universal Serial Bus (USB).

Since the relay lens and focusing module used in the conventional fixation light element are omitted, the ophthalmoscope of the present invention has a very compact structure. In one embodiment, the ophthalmoscope of the present invention further comprises a housing whose shape is easy to be handheld, such as the shape of a pistol. The ophthalmoscope of the present invention can be fabricated into a handheld device via arranging the illumination element 11, the imaging lens group, the image capture module 13 and other necessary components inside the housing.

In conclusion, the present invention makes the image sensing element and the fixation light element situated on the equivalent focal planes of the imaging lens group by using appropriate optical elements (such as a prism group or an optical splitter). In other words, the fixation light element shares the lens group and focusing mechanism with the imaging system to project the fixation light beam to the fundus of the eyeball. Therefore, the relay lens and focusing module used by the conventional fixation light element may be omitted and the present invention can reduce the volume of an ophthalmoscope and decrease the assemblage complexity thereof.

The embodiments described above are to demonstrate the technical thought and characteristics of the present invention to enable the persons skilled in the art to understand, make, and use the present invention. However, these embodiments are only to exemplify the present invention but not to limit the scope of the present invention. Any equivalent modification or variation according to the spirit of the present invention is to be also included within the scope of the present invention.

What is claimed is:

1. An ophthalmoscope, comprising
an illumination element configured for providing an illumination light beam passing through a pupil of an eyeball and reaching a fundus of said eyeball;
an imaging lens group configured for converging a reflected light beam from said fundus of said eyeball; and
an image capture module including
an image sensing element configured for capturing said reflected light beam converged by said imaging lens group to form an image;
a fixation light element configured for providing a fixation light beam passing through said imaging lens group and reaching said fundus of said eyeball, wherein said fixation light element and said image sensing element are arranged at an identical side of said imaging lens group; and
an optical element arranged among said imaging lens group, said image sensing element and said fixation light element, and configured for positioning said image sensing element and said fixation light element on equivalent focal planes of said imaging lens group.

2. The ophthalmoscope according to claim 1, wherein said optical element includes a prism group.

3. The ophthalmoscope according to claim 1, wherein said optical element includes an optical splitter.

4. The ophthalmoscope according to claim 1 further comprising:
a focus adjusting module mechanically or electronically driving said image capture module to move linearly along an optical axis of said imaging lens group.

5. The ophthalmoscope according to claim 1 further comprising
a focus adjusting module driving at least one lens of said image lens group to move linearly along an optical axis of said imaging lens group.

6. The ophthalmoscope according to claim 1, wherein said fixation light element includes either of a first LED (Light Emitting Diode) and a light sensing element and at least four second LEDs (Light Emitting Diodes), and said second LEDs are arranged annularly and symmetrically about said first LED or said light sensing element.

7. The ophthalmoscope according to claim 1, wherein said fixation light element includes either of a first LED (Light Emitting Diode) and a light sensing element and six second LEDs, and wherein said six second LEDs are arranged annularly and symmetrically about said first LED or said light sensing element.

8. The ophthalmoscope according to claim 1, wherein said imaging lens group has a first lens group and a second lens group, and wherein said illumination light beam passes through said first lens group and reaches said fundus of said eyeball.

9. The ophthalmoscope according to claim 8, wherein a position of said illumination element and a position of said pupil meet an image-object relationship with respect to said first lens group.

10. The ophthalmoscope according to claim 1, wherein a light path of said illumination element is deviated from an optical axis of said imaging lens group.

11. The ophthalmoscope according to claim 1, wherein said illumination element is an annular light emitting element or includes a plurality of light emitting elements arranged annularly and symmetrically.

12. The ophthalmoscope according to claim 1, wherein said illumination element includes a plurality of first LEDs (Light Emitting Diodes) and a plurality of second LEDs, said first LEDs are symmetrically and annularly arranged, and said second LEDs are also symmetrically and annularly arranged, and wherein a central wavelength of light emitted by said first LEDs is different from a central wavelength of light emitted by of said second LEDs.

13. The ophthalmoscope according to claim 1 further comprising
a display module configured for displaying images captured by said image capture module.

14. The ophthalmoscope according to claim 1 further comprising
a connection port physically connected with an external electronic device to transmit images captured by said image capture module to said external electronic device.

15. The ophthalmoscope according to claim 1 further comprising
a memory unit configured for recording images captured by said image capture module.

16. The ophthalmoscope according to claim 1 further comprising
a housing whose shape having a shape designed for handheld, wherein said illumination element, said imaging lens group and said image capture module are arranged inside said housing to form a handheld device.

* * * * *